United States Patent [19]
Hanson

[11] Patent Number: 5,769,702
[45] Date of Patent: Jun. 23, 1998

[54] VARIABLE POSITIONING GASEOUS CONDUIT ORIFICE AND METHOD OF USE

[75] Inventor: Sean P. Hanson, Salt Lake City, Utah

[73] Assignee: Sorenson Critical Care, Inc., West Jordan, Utah

[21] Appl. No.: 593,145

[22] Filed: Feb. 1, 1996

[51] Int. Cl.[6] .................................................... B08B 15/04
[52] U.S. Cl. ....................... 454/63; 128/204.18; 454/66; 604/313; 604/902
[58] Field of Search ................................. 454/63, 65, 66; 604/313, 902; 128/200.28, 204.18; 118/224

[56] References Cited

U.S. PATENT DOCUMENTS

| | | |
|---|---|---|
| 876,766 | 1/1908 | Blaisdell . |
| 1,148,093 | 7/1915 | Kells . |
| 1,755,151 | 4/1930 | Henderson . |
| 1,994,091 | 1/1935 | Lutz ........................................ 128/360 |
| 2,115,482 | 4/1938 | Crewe ................................... 454/63 X |
| 3,308,825 | 3/1967 | Cruse ..................................... 128/276 |
| 3,374,856 | 3/1968 | Wirt ....................................... 181/224 |
| 4,002,170 | 1/1977 | Hansen et al. ......................... 128/276 |
| 4,068,664 | 1/1978 | Sharp et al. ............................ 128/276 |
| 4,230,114 | 10/1980 | Feather .................................. 128/293 |
| 4,282,869 | 8/1981 | Zidulka .............................. 128/200.28 |
| 4,307,720 | 12/1981 | Weber, Jr. .............................. 128/276 |
| 4,407,280 | 10/1983 | Trammell et al. ..................... 128/205 |
| 5,181,916 | 1/1993 | Reynolds et al. ........................ 606/16 |
| 5,380,245 | 1/1995 | Reiterman et al. ...................... 454/63 |
| 5,395,278 | 3/1995 | Dickhut ................................. 446/486 |
| 5,427,570 | 6/1995 | Chen ...................................... 454/65 |
| 5,461,200 | 10/1995 | Norcia ................................... 174/135 |
| 5,548,093 | 8/1996 | Sato et al. .............................. 181/224 |
| 5,597,385 | 1/1997 | Moerke .................................... 55/274 |

FOREIGN PATENT DOCUMENTS

| | | |
|---|---|---|
| 197710 | 8/1967 | U.S.S.R. . |
| 559074 | 8/1977 | U.S.S.R. . |
| 2 169 515A | 7/1986 | United Kingdom . |
| WO 85/05277 | 12/1985 | WIPO . |

OTHER PUBLICATIONS

Sherwood Medical, Lighthouse Tip Vena Caval Catheters, Product Brochure, date unknown.

Black & Decker, Snake Light, Product Advertisement, date unknown.

*Primary Examiner*—Harold Joyce
*Attorney, Agent, or Firm*—Madson & Metcalf

[57] ABSTRACT

A selectively positionable fluid conduit for gas removal from or gas introduction to a specific environment is disclosed. The fluid conduit includes a tubular wand having an orifice at the distal end thereof. Unwanted gases are removed by suction force through the orifice. Desirable or therapeutic gases are introduced to a specific location through the orifice. The tubular wand is coupled to a malleable positioning tube. The malleable positioning tube can be manipulated into various configurations such that the positioning tube maintains the last chosen configuration. In one disclosed embodiment, the malleable positioning tube includes tubular bellows formed from a plurality of alternating large and small diameter rings joined by frusto-conical walls. In another embodiment, the malleable positioning tube includes a malleable wire associated with a semi-rigid tube. Interaction between the rings and the frusto-conical walls imparts malleable properties to the positioning tube. A flexible liner located within the malleable positioning tube can provide a smooth surface which eliminates whistling caused by gas flow through the tube. The malleable positioning tube is in gaseous communication with either a gas evacuator or to a pressurized gas source. In one disclosed embodiment, a flexible tube is used to connect the malleable positioning tube to a gas evacuator or gas source.

39 Claims, 4 Drawing Sheets

VARIABLE POSITIONING GASEOUS CONDUIT ORIFICE AND METHOD OF USE

BACKGROUND

1. Field of the Invention

The present invention is directed to an apparatus and method for introduction of therapeutic gases to or evacuation of fumes from a selected environment. More particularly, the invention permits variable positioning of the orifice of a gaseous fluid conduit for the introduction or evacuation of gases.

2. Technology Background

There are many instances where it is desirable to evacuate smoke, fumes, unwanted gases, or debris from a specific location. Similarly, there is often the need to introduce therapeutic gases to a specific location.

Surgical plume evacuation technology typically involves a vacuum source attached to a conduit which removes smoke from a distal surgical site. Filters are commonly used within the conduit or vacuum source to filter particles and odor. A variety of structures located at the distal end are known to provide a barrier or screen against entry of sponges, gauze, or other large debris into the evacuation system. One such example is disclosed in U.S. Pat. No. 5,380,245 to Reiterman et al. Other structures are designed to enhance the suction force through creation of a vortex, such as those described in U.S. Pat. Nos. 5,181,916 to Reynolds et al. and 5,192,267 to Shapira et al.

Historically, medical personnel have manually held the orifice of an evacuation wand at the appropriate location and position during laser or electrocautery surgery. Because of increased emphasis on reducing surgery costs, there is a need in the art for plume evacuators which do not require a medical professional to hold the evacuation wand near the surgical site during surgery.

Some smoke evacuator systems have incorporated auxiliary positioning devices to affix the location of the distal orifice at or near the treatment site. Such devices are large metal structures that must be cleaned, lubricated, and sterilized after each use. Such auxiliary devices are prohibitively expensive.

Known positive pressure gaseous fluid delivery systems also have shortcomings with regard to expense and problems of reuse. One such therapeutic gas delivery system is disclosed in U.S. Pat. No. 4,407,280 to Trammell et al. Instead of localized, site-specific delivery of gases, this system relies on containment of delivered gases within a hood in which exhaled breath is also accumulated. The exhaled gases intermix with the newly delivered gases and dilute the therapeutic potential of the delivered gases. Also, newly delivered gases are wastefully vented outside the hood with the exhaled gases.

Another significant problem associated with air-flow conduits having accordion-like corrugation along the conduit walls is the generation of a whistling sound when air flows through the conduit.

It would be an advancement in the art to provide a disposable suction or positive pressure orifice positioning device which is inexpensive and enables reliable single procedure relocation and positioning of the orifice as well as safe disposal. It would be another advancement in the art to provide an air-flow conduit which eliminates whistling when air flows through the conduit.

SUMMARY

The present invention is directed to a selectively positionable orifice of a gaseous fluid conduit for gas removal from or gas introduction to a specific environment. A currently preferred embodiment includes a tubular wand having a distal end, a proximal end, and an orifice at the distal end thereof. Unwanted gases are removed by suction force through the orifice. Particulates and odor are removed using known filtering techniques usually associated with the suction source. Desirable or therapeutic gases are introduced to a specific location through the orifice.

The proximal end of the tubular wand is attached to the distal end of a malleable positioning tube. The malleable positioning tube can be manipulated into various configurations such that the positioning tube maintains the last chosen configuration. In a presently preferred embodiment the malleable positioning tube includes tubular bellows formed from a plurality of alternating large and small diameter rings joined by frusto-conical walls. Interaction between the rings and the frusto-conical walls imparts malleable properties to the positioning tube. Other means can also be used to render the positioning tube malleable, such as a malleable wire affixed to or associated with the positioning tube. The malleable positioning tube is preferably fabricated of a semi-rigid material such as elastomeric or polymeric materials, compressed paper or glass fibers, or similar material.

The proximal end of the malleable positioning tube is preferably attached to a flexible tube. The flexible tube is configured for attachment to either a gas evacuator or to a pressurized gas source. In one currently preferred embodiment, the flexible tube is configured for attachment to a surgical smoke evacuator. The flexible tube is preferably fabricated of conventional tubing having a size comparable to the positioning tube. The flexible tube typically has a cross sectional diameter in the range from about 0.1 inch to 3 inches, and more preferably from about 0.75 inch to 1.5 inch. The flexible tube can include ribs, or a similar structure, to provide dimensional stability and strength for gas evacuation or gas introduction applications.

The selectively positionable gaseous fluid conduit according to the present invention preferably includes means for eliminating whistling caused by gas flow through the malleable positioning tube. For instance, a flexible liner located within the malleable positioning tube can provide a smooth surface which eliminates whistling caused by gas flow through the malleable positioning tube. A sponge blocker can also be provided to prevent sponges, wipe pads, and other foreign debris from entering the positioning tube.

DETAILED DESCRIPTION OF THE PREFERRED EMBODIMENTS

Figure 1:
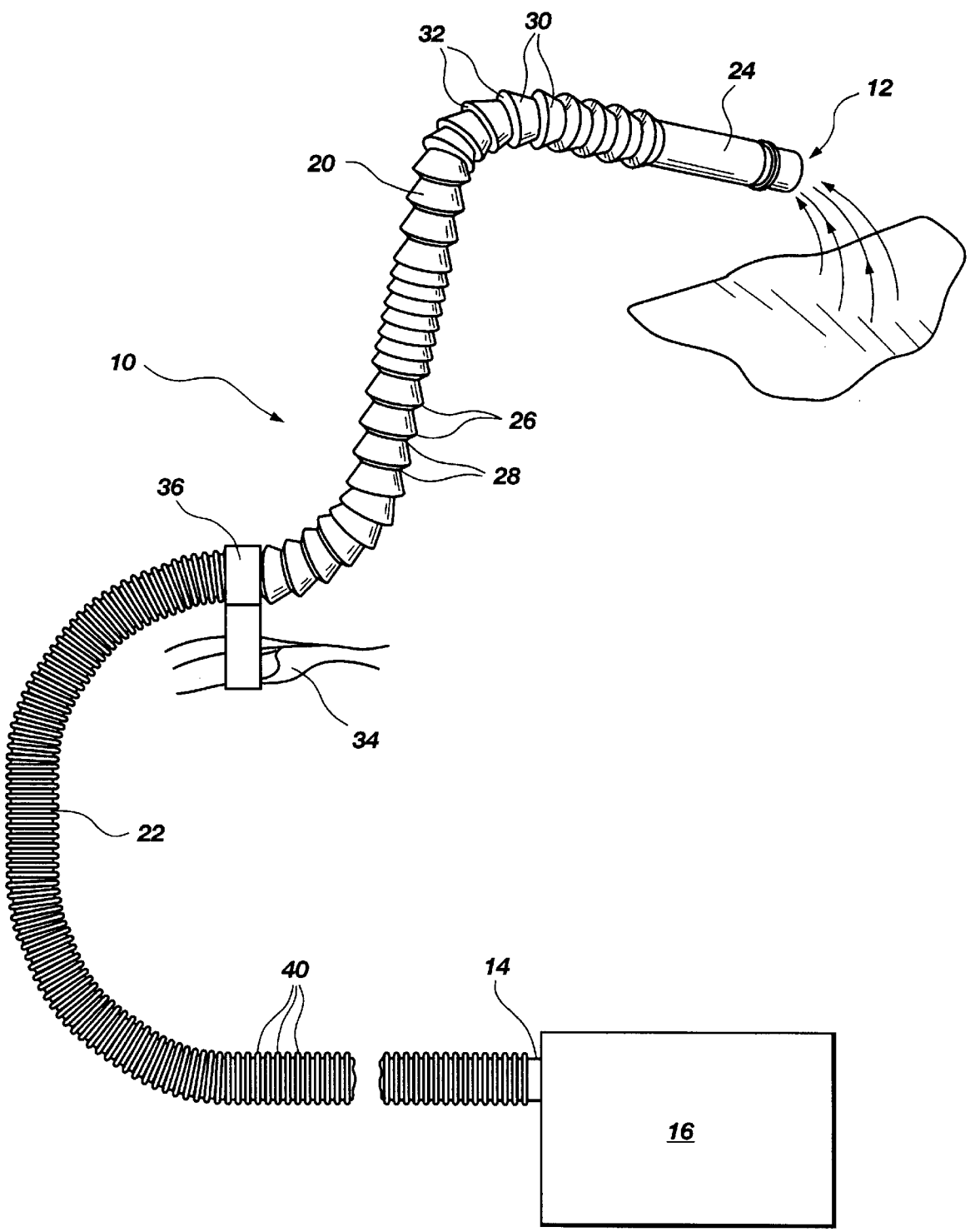
FIG. 1 is a perspective view of a variable positioning gaseous conduit orifice within the scope of the present invention.

Reference is now made to the figures wherein like parts are referred to by like numerals throughout. With particular reference to FIG. 1, a gaseous fluid conduit 10 is disclosed. The fluid conduit can be used for gas removal from or gas introduction to a specific environment. The fluid conduit 10 is sized to allowed gases to flow through the conduit. An orifice 12 is located at the distal end of the fluid conduit 10. Unwanted gases are removed by suction force through the orifice 12. Desirable or therapeutic gases are introduced to a specific location through the orifice 12. The proximal end 14 of the fluid conduit 10 is configured for attachment to means for providing a gas flow driving force 16, such as a gas evacuator or a pressurized gas source. A standard connector can be used for this purpose.

The fluid conduit 10 shown in FIG. 1 includes a malleable positioning tube 20 and a flexible tube 22. A tubular wand 24 is located between the orifice 12 and the malleable positioning tube 20. The tubular wand 24 can have various lengths ranging from less than one inch to several inches.

Figure 3:
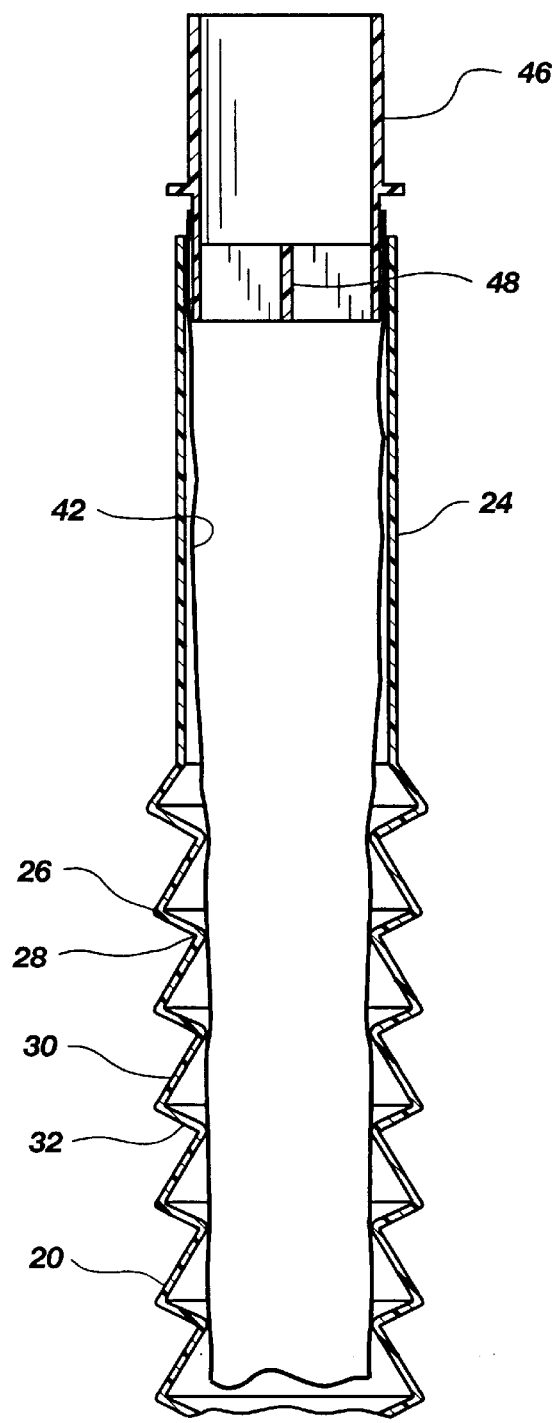
FIG. 3 is a cross sectional view of the distal end of a variable positioning gaseous conduit orifice within the scope of the present invention having accordion-like corrugation along a portion of the conduit.
Figure 4:
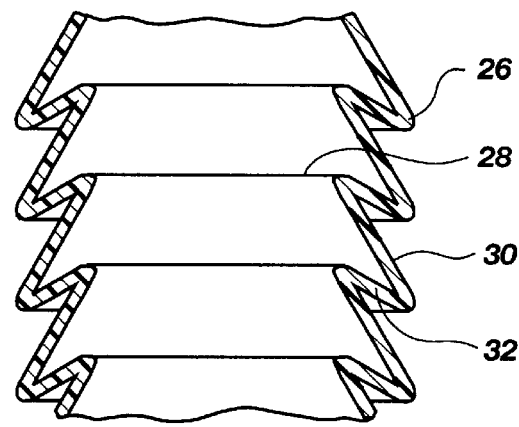
FIG. 4 is an enlarged cross sectional view of accordion-like corrugations in a contracted configuration.

The malleable positioning tube 20 can be manipulated into various configurations such that the positioning tube maintains the last chosen configuration. In this manner, the orifice 12 can be selectively positioned and retained in a desired location. In a presently preferred embodiment, the malleable positioning tube 20 includes accordion-like, tubular bellows formed from a plurality of alternating large diameter rings 26 and small diameter rings 28 joined by frusto-conical walls 30, 32. Interaction between the rings 26, 28 and the frusto-conical walls 30, 32 imparts malleable properties to the positioning tube 20. FIG. 3 illustrates the tubular bellows in an extended configuration, while FIG. 4 illustrates the tubular bellows in a contracted configuration.

Other means can also be used to render the positioning tube malleable, such as one or more malleable wires affixed to the positioning tube. Several possible configurations of the positioning tube having a malleable wire associated therewith are illustrated in FIGS. 5–9. The malleable positioning tube is preferably fabricated of a semi-rigid material such as elastomeric or polymeric materials, compressed paper or glass fibers, or equivalent material. Although the malleable positioning tube is illustrated in the figures with a circular cross sectional configuration, other geometric configurations are within the scope of the present invention including oval and other geometric shapes.

In use, the fluid conduit 10 is preferably attached to a support structure 34 with a clamp 36. The clamp 36 can be any of a number of commercially available clamps used in the medical field. In the illustrated embodiment, the support structure 34 is a cloth or fabric material, such as a bed cover, drape, or curtain. Of course, one skilled in the art is capable of attaching the fluid conduit to other structures, including non-cloth surfaces, depending on the circumstances.

In the embodiment shown in FIG. 1, the proximal end of the malleable positioning tube 20 is attached to the flexible tube 22. The flexible tube 22 is configured for attachment to either a gas evacuator or to a pressurized gas source 16. In a currently preferred embodiment, the flexible tube 22 is configured for attachment to a surgical smoke evacuator 16. The flexible tube 22 is preferably fabricated of conventional tubing having a size comparable to the positioning tube 20. The flexible tube 22 typically has a cross sectional diameter in the range from 0.1 inch to 3 inches and preferably from 0.75 inch to 1.5 inch. Standard ⅞ inch or 1¼ inch tubing are currently preferred. The flexible tube 22 can include ribs 40, or a similar structure, to provide dimensional stability and strength for gas evacuation or gas introduction applications.

The malleable positioning tube 20 can be removably attached to the flexible tube 22 with a coupling device (not shown) to facilitate removal and replacement of the positioning tube 20.

Figure 2:
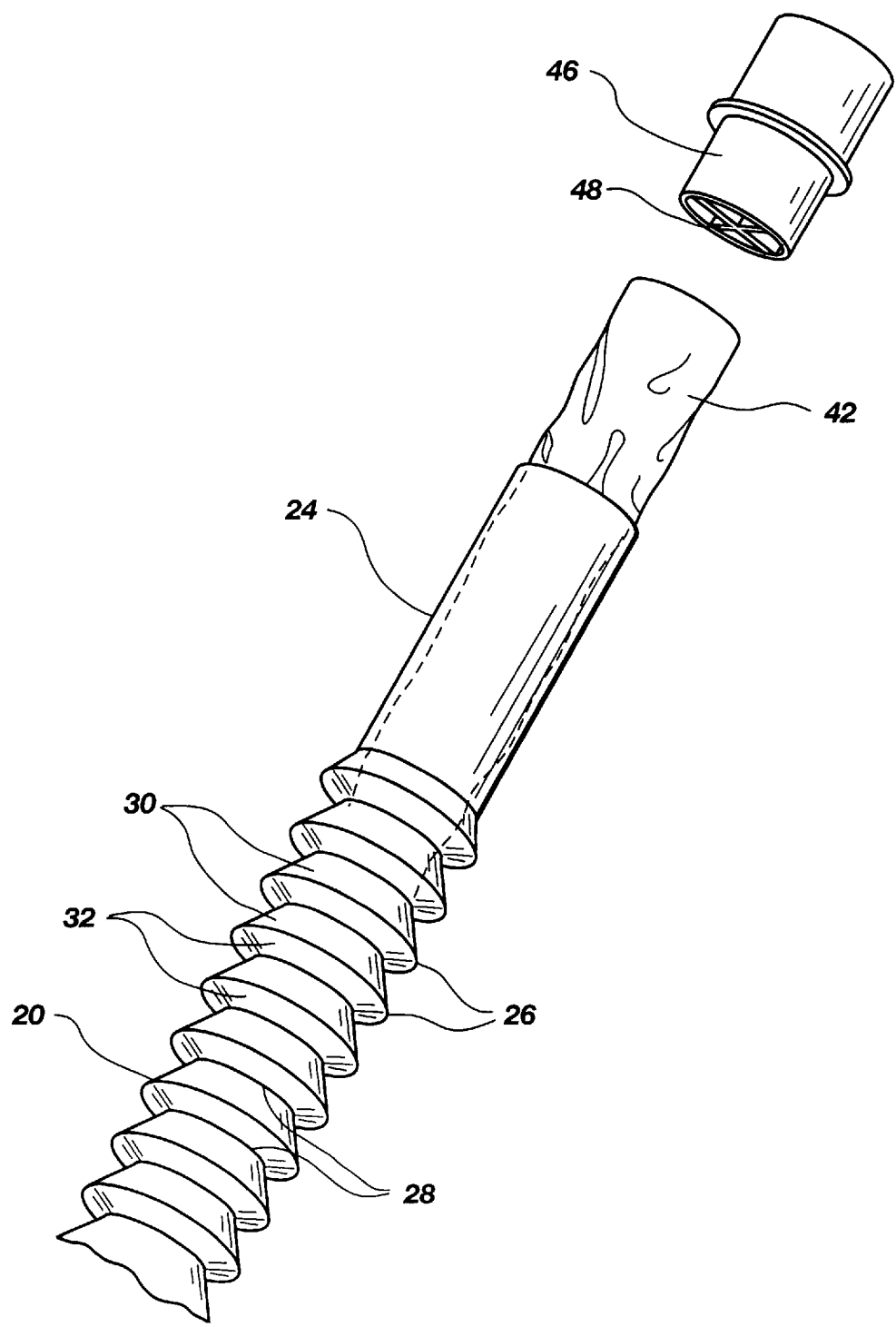
FIG. 2 is a partially exploded perspective view of the distal end of a variable positioning gaseous conduit orifice within the scope of the present invention.

When the malleable positioning tube 20 has an accordion-like structure, gaseous fluid flow through the tube can cause a whistling sound. In such cases, the fluid conduit 10 preferably includes means for eliminating whistling caused by gas flow through the malleable positioning tube 20. As shown in FIGS. 2 and 3, a flexible liner 42 located within the malleable positioning tube 20 can provide a smooth surface which eliminates whistling caused by gas flow through the malleable positioning tube. The liner 42 is preferably fabricated of cloth or a flexible, thin plastic. The liner can also be fabricated of a thin, porous sponge material, optionally impregnated with charcoal particles for odor control. The liner 42 is preferably anchored near the distal end of the fluid conduit 10 with a coupling, clamp or bond. The whistling sound can be eliminated by other methods, such as increasing the diameter of the malleable positioning tube or altering the interior geometry of the positioning tube.

If the fluid conduit 10 is used to evacuate smoke, fumes, or debris, a sponge blocker 46 is preferably provided to screen sponges, wipe pads, and other large foreign debris inadvertently suctioned into the fluid conduit 10. The sponge blocker 46 illustrated in FIGS. 2 and 3 is located at the orifice 12 of the fluid conduit 10. However, it will be appreciated that the sponge blocker 46 can be located elsewhere within the fluid conduit. The sponge blocker 46 preferably includes one or more vanes 48 extending inward towards the center of the conduit. The sponge blocker 46 can be constructed of a variety of materials, including various plastics such as clear polycarbonate. When the fluid conduit 10 is configured for use in evacuation of smoke from electrocautery or laser surgery, the sponge blocker 46 preferably includes a flame retardant ingredient. The flame retardant advantageously prevents inadvertent ignition of the sponge blocker during electrocautery or laser surgery.

In the embodiment illustrated in FIGS. 2 and 3, the sponge blocker 46 is configured to press fit within the tubular wand 24. The sponge blocker 46 can also be used to anchor the flexible liner 42 in position within the positioning tube 20. This is accomplished by placing the sponge blocker 46 within the flexible liner 42 and then press-fitting the sponge blocker 46 within the tubular wand 24. In this manner, the flexible liner 42 is pressed between the sponge blocker 46 and the tubular wand 24.

Figure 5:
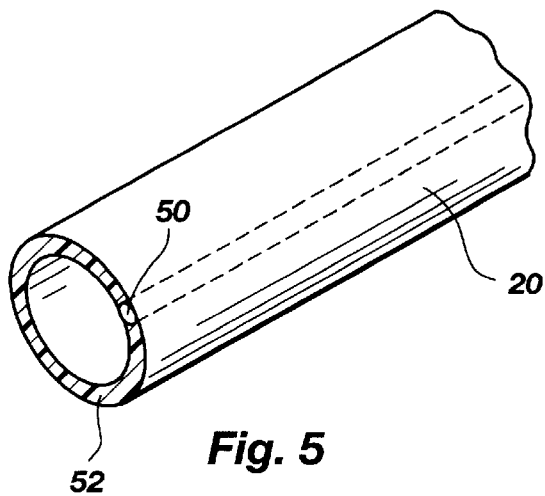
FIG. 5 is a cross sectional perspective view of a malleable positioning tube within the scope of the present invention containing a malleable wire integral with the tube wall.
Figure 6:
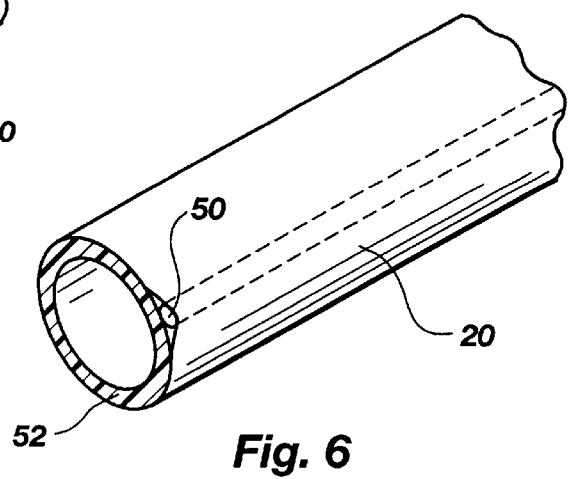
FIG. 6 is a cross sectional perspective view of a malleable positioning tube within the scope of the present invention containing a malleable wire affixed to and exterior of the tube wall.
Figure 7:
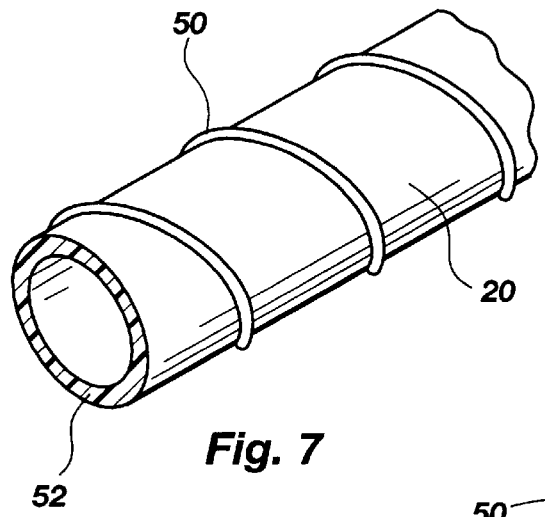
FIG. 7 is a cross sectional perspective view of a malleable positioning tube within the scope of the present invention containing a malleable wire wrapped about the exterior surface of the tube wall.
Figure 8:
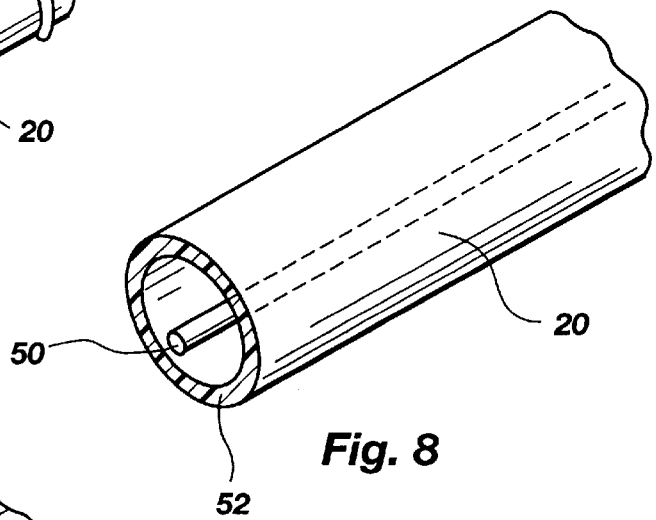
FIG. 8 is a cross sectional perspective view of a malleable positioning tube within the scope of the present invention containing a malleable wire located within the center of the tube.

FIGS. 5–9 illustrate several embodiments of the malleable positioning tube 20 having a malleable wire 50 associated therewith. The embodiment illustrated in FIG. 5 shows the malleable wire 50 integral with the tube wall 52. This embodiment can be fabricated using know extrusion techniques. FIG. 6 shows the malleable wire 50 extending longitudinally along the exterior surface of the tube wall 52. FIG. 7 shows the malleable wire 50 wrapped about the exterior surface of the tube wall 52. FIG. 8 shows the malleable wire 50 located within the interior of the positioning tube 20.

Figure 9:
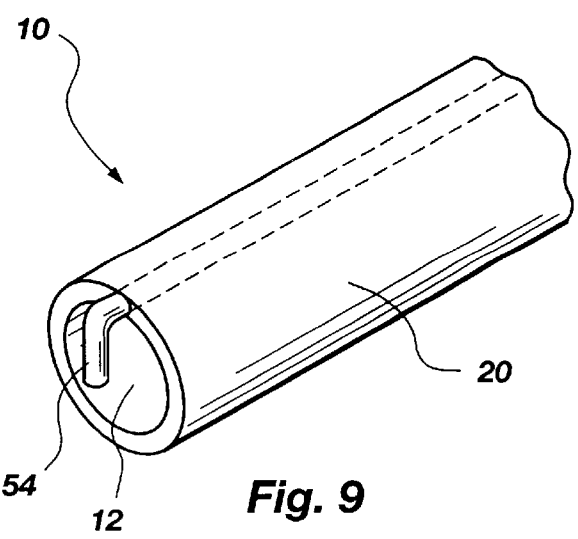
FIG. 9 is a perspective view of the distal end of a variable positioning gaseous conduit orifice having a cross sectional configuration similar to that of FIG. 5 in which the distal end of the malleable wire is stripped of tube material and bent over the orifice to function as a sponge blocker.

FIG. 9 shows the distal end of the orifice 12 of a fluid conduit 10 having a positioning tube 20 with a cross sectional configuration similar to that of FIG. 5 in which the distal end of the malleable wire 54 is stripped of tube material and bent over the orifice 12 to function as a sponge blocker. As shown in FIG. 9, the fluid conduit 10 does not always have a tubular wand.

It will be appreciated that the present invention may be utilized as a conduit to deliver fluids under positive pressure or high-velocity negative pressure to a selected site. Examples of use include, for example, evacuation of surgical plume from an electrocautery or laser site, evacuation of diseased toenail or fingernail particles or nail polish fumes during podiatric grinding and medication treatments, ventilation of epoxy resin fumes during dental procedures, evacuation of solvent bonding fumes in clean rooms, introduction of therapeutic gases more site-specifically to the vicinity of a patient's nose or mouth and introduction of desired gases to maintain relative gaseous balance in a designated ambient environment.

It should be appreciated that the variable positioning gaseous conduit orifice and method of use according to the present invention are capable of being incorporated in the form of a variety of embodiments, only a few of which have been illustrated and described above. The invention may be embodied in other forms without departing from its essential characteristics. The described embodiments are to be considered in all respects only as illustrative and not restrictive and the scope of the invention is, therefore, indicated by the appended claims rather than by the foregoing description.

What is claimed is:

1. A selectively positionable gaseous fluid conduit for gas removal from or introduction to a specific environment comprising:
    an orifice;
    a malleable positioning tube having a proximal end and a distal end, wherein the distal end of the positioning tube is in gaseous communication with the orifice, wherein the malleable positioning tube can be manipulated into various configurations, wherein the malleable positioning tube comprises tubular bellows formed from a plurality of alternating large and small diameter rings joined by frusto-conical walls, and wherein the positioning tube maintains the last chosen configuration; and
    a flexible tube having a proximal end and a distal end, wherein the distal end of the flexible tube is attached to the proximal end of the positioning tube, and wherein the proximal end of the flexible tube is configured for attachment to either a gas evacuator or to a pressurized gas source.

2. A selectively positionable gaseous fluid conduit as defined in claim 1, wherein the flexible tube is configured for attachment to a surgical smoke evacuator.

3. A selectively positionable gaseous fluid conduit as defined in claim 2, wherein the surgical smoke evacuator includes at least one filter from removal of particulates and odor.

4. A selectively positionable gaseous fluid conduit as defined in claim 1, wherein the flexible tube is configured for attachment to a source of pressurized therapeutic gas.

5. A selectively positionable gaseous fluid conduit as defined in claim 1, further comprising a tubular wand having a distal end and a proximal end, wherein the orifice is located at the distal end thereof and wherein the proximal end of the tubular wand is attached to the distal end of the positioning tube.

6. A selectively positionable gaseous fluid conduit as defined in claim 1, wherein the malleable positioning tube is fabricated of a semi-rigid polymeric material.

7. A selectively positionable gaseous fluid conduit as defined in claim 1, wherein the flexible tube has a cross sectional diameter in the range from 0.1 inch to 3 inches.

8. A selectively positionable gaseous fluid conduit as defined in claim 1, wherein the flexible tube has a cross sectional diameter in the range from 0.75 inch to 1.5 inch.

9. A selectively positionable gaseous fluid conduit as defined in claim 1, further comprising means for eliminating whistling caused by gas flow through the malleable positioning tube.

10. A selectively positionable gaseous fluid conduit as defined in claim 1, further comprising a liner located within the malleable positioning tube for eliminating whistling caused by gas flow through the malleable positioning tube.

11. A selectively positionable gaseous fluid conduit as defined in claim 10 wherein the liner is fabricated of a material impregnated with charcoal.

12. A selectively positionable air evacuation wand for use in combination with an air evacuator for removing air and entrained smoke, fumes, or debris from an environment comprising:
    a tubular wand having a distal end, a proximal end, and an orifice at the distal end thereof;
    a malleable positioning tube having a proximal end and a distal end, wherein the distal end of the positioning tube is attached to the proximal end of the tubular wand, wherein the malleable positioning tube can be manipulated into various configurations, wherein the malleable positioning tube comprises a malleable wire associated with a semi-rigid tube, and wherein the positioning tube maintains the last chosen configuration; and
    a flexible tube having a proximal end and a distal end, wherein the distal end of the flexible tube is attached to the proximal end of the positioning tube, and wherein the proximal end of the flexible tube is configured for attachment to the air evacuator.

13. A selectively positionable air evacuation wand as defined in claim 12, wherein the malleable positioning tube is fabricated of a semi-rigid polymeric material.

14. A selectively positionable air evacuation wand as defined in claim 12, wherein the flexible tube has a cross sectional diameter in the range from 0.1 inch to 3 inches.

15. A selectively positionable air evacuation wand as defined in claim 12, wherein the flexible tube has a cross sectional diameter in the range from 0.75 inch to 1.5 inch.

16. A selectively positionable air evacuation wand as defined in claim 12, further comprising means for eliminating whistling caused by air flow through the malleable positioning tube.

17. A selectively positionable air evacuation wand as defined in claim 12, further comprising a liner located within the malleable positioning tube for eliminating whistling caused by air flow through the malleable positioning tube.

18. A selectively positionable air evacuation wand as defined in claim 17, wherein the liner is fabricated of a material impregnated with charcoal.

19. A selectively positionable air evacuation wand as defined in claim 12, wherein the air evacuator is a surgical smoke evacuator for removing smoke from a surgical environment.

20. A selectively positionable air evacuation wand as defined in claim 19, wherein the tubular wand further comprises a sponge blocker.

21. A selectively positionable air evacuation wand as defined in claim 20, wherein the sponge blocker is constructed of a polymeric material comprising a flame retardant.

22. A selectively positionable surgical smoke evacuation orifice for use in combination with a surgical smoke evacuator for removing smoke from a surgical environment comprising:

a tubular wand having a distal end, a proximal end, and an orifice at the distal end thereof, said wand including a sponge blocker constructed of a polymeric material comprising a flame retardant;

a malleable positioning tube fabricated of a semi-rigid polymeric material having a proximal end and a distal end, wherein the distal end of the positioning tube is attached to the proximal end of the tubular wand, wherein the malleable positioning tube can be manipulated into various configurations, wherein the malleable positioning tube comprises tubular bellows formed from a plurality of alternating large and small diameter rings joined by frusto-conical walls, and wherein the positioning tube maintains the last chosen configuration;

a liner located within the malleable positioning tube for eliminating whistling caused by air flow through the malleable positioning tube; and a flexible tube having a proximal end and a distal end, wherein the distal end of the flexible tube is attached to the proximal end of the positioning tube, and wherein the proximal end of the flexible tube is configured for attachment to the surgical smoke evacuator, said flexible tube having a cross sectional diameter in the range from 0.1 inch to 3 inches.

23. A process of evacuating smoke, fume contaminants, or debris from an environment comprising the steps of:

(a) obtaining an air evacuation device having a malleable positioning tube in gaseous communication with an orifice at one end thereof and in gaseous communication with an air evacuator at the other end thereof, wherein the malleable positioning tube can be manipulated into various configurations, wherein the malleable positioning tube comprises tubular bellows formed from a plurality of alternating large and small diameter rings joined by frusto-conical walls, and wherein the positioning tube maintains the last chosen configuration;

(b) removably anchoring the malleable positioning tube to a location near the environment;

(c) manipulating the malleable positioning tube such that the orifice is positioned adjacent a source of smoke, fumes, or debris;

(d) engaging the air evacuator such that smoke, fumes, or debris from the environment are drawn into the orifice, through the malleable positioning tube, and into the air evacuator; and (e) filtering the smoke, fumes, or debris.

24. A process of evacuating smoke, fume contaminants, or debris from an environment as defined in claim 23, wherein the air evacuation device further comprises a liner located within the malleable positioning tube for eliminating whistling caused by air flow through the malleable positioning tube.

25. A process of evacuating smoke, fumes contaminants, or debris from an environment as defined in claim 24, wherein the liner is fabricated of a material impregnated with charcoal.

26. A process of evacuating smoke, fume contaminants, or debris from an environment as defined in claim 23, wherein the air evacuation device further comprises a sponge blocker.

27. A process of introducing therapeutic gas to a location near the mouth or nose of a patient comprising the steps of:

(a) obtaining a therapeutic gas delivery device having a malleable positioning tube in gaseous communication with an orifice at one end thereof and in gaseous communication with a source of pressurized therapeutic gas at the other end thereof, wherein the malleable positioning tube can be manipulated into various configurations, wherein the malleable positioning tube comprises tubular bellows formed from a plurality of alternating large and small diameter rings joined by frusto-conical walls, and wherein the positioning tube maintains the last chosen configuration;

(b) removably anchoring the malleable positioning tube to a location near the patient;

(c) manipulating the malleable positioning tube such that the orifice is positioned near the mouth or nose of the patient; and (d) engaging the source of pressurized therapeutic gas such that therapeutic gas flows through the malleable positioning tube and through the orifice to a location near the mouth or nose of the patient.

28. A process of introducing therapeutic gas to a location near the mouth or nose of a patient as defined in claim 27, wherein the gas delivery device further comprises a liner located within the malleable positioning tube for eliminating whistling caused by gas flow through the malleable positioning tube.

29. A selectively positionable gaseous fluid conduit for gas removal from or introduction to a specific environment comprising:

an orifice;

a malleable positioning tube having a proximal end and a distal end, wherein the distal end of the positioning tube is in gaseous communication with the orifice, wherein the malleable positioning tube can be manipulated into various configurations, wherein the malleable positioning tube comprises a malleable wire associated with a semi-rigid tube, and wherein the positioning tube maintains the last chosen configuration; and a flexible tube having a proximal end and a distal end, wherein the distal end of the flexible tube is attached to the proximal end of the positioning tube, and wherein the proximal end of the flexible tube is configured for attachment to either a gas evacuator or to a pressurized gas source.

30. A selectively positionable gaseous fluid conduit as defined in claim 29, wherein the flexible tube is configured for attachment to a surgical smoke evacuator.

31. A selectively positionable gaseous fluid conduit as defined in claim 30, wherein the surgical smoke evacuator includes at least one filter from removal of particulates and odor.

32. A selectively positionable gaseous fluid conduit as defined in claim 29, wherein the flexible tube is configured for attachment to a source of pressurized therapeutic gas.

33. A selectively positionable gaseous fluid conduit as defined in claim 29, further comprising a tubular wand having a distal end and a proximal end, wherein the orifice is located at the distal end thereof and wherein the proximal end of the tubular wand is attached to the distal end of the positioning tube.

34. A selectively positionable gaseous fluid conduit as defined in claim 29, wherein the malleable positioning tube is fabricated of a semi-rigid polymeric material.

35. A selectively positionable gaseous fluid conduit as defined in claim 29, wherein the flexible tube has a cross sectional diameter in the range from 0.1 inch to 3 inches.

36. A selectively positionable gaseous fluid conduit as defined in claim 29, wherein the flexible tube has a cross sectional diameter in the range from 0.75 inch to 1.5 inch.

37. A selectively positionable gaseous fluid conduit as defined in claim 29, further comprising means for eliminating whistling caused by gas flow through the malleable positioning tube.

38. A selectively positionable gaseous fluid conduit as defined in claim 29, further comprising a liner located within the malleable positioning tube for eliminating whistling caused by gas flow through the malleable positioning tube.

39. A selectively positionable gaseous fluid conduit as defined in claim 38, wherein the liner is fabricated of a material impregnated with charcoal.

\* \* \* \* \*